US011071703B2

(12) United States Patent
Mathonneau et al.

(10) Patent No.: US 11,071,703 B2
(45) Date of Patent: *Jul. 27, 2021

(54) COSMETIC COMPOSITION COMPRISING A COMBINATION OF ANIONIC SURFACTANTS OF CARBOXYLATE AND ACYLISETHIONATE TYPE

(71) Applicant: L'OREAL, Paris (FR)

(72) Inventors: Estelle Mathonneau, Paris (FR);
Marie-Florence D'Arras, Clichy (FR);
Jean-Michel Sturla, Boulogne (FR);
Virginie Le Chaux, Franconville (FR);
Lydia Dussault, Saint Nom la Breteche (FR)

(73) Assignee: L'OREAL, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/024,144

(22) PCT Filed: Sep. 19, 2014

(86) PCT No.: PCT/EP2014/070050
§ 371 (c)(1),
(2) Date: Mar. 23, 2016

(87) PCT Pub. No.: WO2015/044056
PCT Pub. Date: Apr. 2, 2015

(65) Prior Publication Data
US 2016/0235639 A1    Aug. 18, 2016

(30) Foreign Application Priority Data
Sep. 24, 2013 (FR) ...................................... 1359190

(51) Int. Cl.
A61K 8/60     (2006.01)
A61Q 5/02     (2006.01)
A61K 8/42     (2006.01)
A61K 8/46     (2006.01)
A61K 8/44     (2006.01)
A61K 8/891    (2006.01)

(52) U.S. Cl.
CPC ............... A61K 8/42 (2013.01); A61K 8/44 (2013.01); A61K 8/442 (2013.01); A61K 8/466 (2013.01); A61K 8/604 (2013.01); A61K 8/891 (2013.01); A61Q 5/02 (2013.01); A61K 2800/30 (2013.01); A61K 2800/596 (2013.01)

(58) Field of Classification Search
None
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,227,615 A | 1/1966 | Korden |
| 3,472,840 A | 10/1969 | Stone et al. |
| 3,589,978 A | 6/1971 | Kamal et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |

(Continued)

FOREIGN PATENT DOCUMENTS

| | | |
|---|---|---|
| CA | 1069522 A1 | 8/1980 |
| EP | 0080976 A1 | 6/1983 |

(Continued)

OTHER PUBLICATIONS

International Search Report for PCT/EP2014/070051 (dated Dec. 3, 2014).
International Search Report for PCT/EP2014/070050 (dated Dec. 8, 2014).
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
Non-Final Office Action for copending U.S. Appl. No. 15/024,140, dated Oct. 19, 2018.
Final Office Action for co-pending U.S. Appl. No. 15/024,140, dated Jul. 25, 2019.

(Continued)

Primary Examiner — Tigabu Kassa
(74) Attorney, Agent, or Firm — The Marbury Law Group, PLLC

(57) ABSTRACT

The invention relates to a cosmetic composition comprising: —one or more anionic surfactants of carboxylate type, chosen from the compounds of formula (I), in a content of greater than or equal to 3% by weight relative to the total weight of the composition, and—one or more anionic surfactants of (C8-C22) acylisethionate type, in a content ranging from 2.5% to 8% by weight relative to the total weight of the composition. This composition is intended for the cosmetic treatment of keratin materials, and in particular for washing the hair. It has excellent foaming power.

20 Claims, No Drawings

(56) References Cited

U.S. PATENT DOCUMENTS

| | | |
|---|---|---|
| 4,075,136 A | 2/1978 | Schaper |
| 4,131,576 A | 12/1978 | Iovine et al. |
| 4,165,367 A | 8/1979 | Chakrabarti |
| 4,166,894 A | 9/1979 | Schaper |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,579,732 A | 4/1986 | Grollier et al. |
| 4,591,610 A | 5/1986 | Grollier |
| 4,608,250 A | 8/1986 | Jacquet et al. |
| 4,719,099 A | 1/1988 | Grollier et al. |
| 4,761,273 A | 8/1988 | Grollier et al. |
| 4,777,040 A | 10/1988 | Grollier et al. |
| 4,839,166 A | 6/1989 | Grollier et al. |
| 4,948,579 A | 8/1990 | Jacquet et al. |
| 4,970,066 A | 11/1990 | Grollier et al. |
| 4,996,059 A | 2/1991 | Grollier et al. |
| 5,009,880 A | 4/1991 | Grollier et al. |
| 5,089,252 A | 2/1992 | Grollier et al. |
| 5,196,189 A | 3/1993 | Jacquet et al. |
| 5,490,955 A | 2/1996 | Hagan et al. |
| 5,958,392 A | 9/1999 | Grollier et al. |
| 6,001,787 A | 12/1999 | Pratley |
| 6,395,692 B1 | 5/2002 | Jaworski et al. |
| 6,565,863 B1 | 5/2003 | Guillou et al. |
| 2007/0081953 A1 | 4/2007 | Dahms |
| 2011/0245126 A1 | 10/2011 | Tsaur et al. |
| 2013/0034515 A1* | 2/2013 | Stone ............... A61Q 5/02 424/70.122 |
| 2014/0112879 A1* | 4/2014 | Molenda ............... A61K 8/42 424/70.19 |

FOREIGN PATENT DOCUMENTS

| | | |
|---|---|---|
| EP | 0122324 A1 | 10/1984 |
| EP | 0337354 A1 | 10/1989 |
| FR | 1492597 A | 8/1967 |
| FR | 1583363 A | 10/1969 |
| FR | 2077143 A | 10/1971 |
| FR | 2080759 A1 | 11/1971 |
| FR | 2162025 A1 | 7/1973 |
| FR | 2190406 A2 | 2/1974 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2383660 A1 | 10/1978 |
| FR | 2393573 A1 | 1/1979 |
| FR | 2413907 A1 | 8/1979 |
| FR | 2470596 A1 | 6/1981 |
| FR | 2505348 A1 | 11/1982 |
| FR | 2519863 A1 | 7/1983 |
| FR | 2542997 A1 | 9/1984 |
| FR | 2598611 A1 | 11/1987 |
| GB | 1546809 A | 5/1979 |
| WO | 2015/044057 A1 | 4/2015 |

OTHER PUBLICATIONS

Non-Final Office Action for co-pending U.S. Appl. No. 15/024,140, dated Feb. 6, 2020.

Final Office Action for copending U.S. Appl. No. 15/024,140, dated Oct. 16, 2020.

\* cited by examiner

COSMETIC COMPOSITION COMPRISING A COMBINATION OF ANIONIC SURFACTANTS OF CARBOXYLATE AND ACYLISETHIONATE TYPE

CROSS REFERENCE TO RELATED APPLICATIONS

This is a national stage application of PCT/EP2014/070050, filed internationally on Sep. 19, 2014, which claims priority to French Application No. 1359190, which was filed on Sep. 24, 2013, both of which are incorporated by reference herein in their entireties.

The present invention relates to a cosmetic composition in particular for washing keratin materials, which comprises a particular combination of anionic surfactants, one of which is of carboxylate type and the other of (C8-C22)acylisethionate type.

The invention also relates to a cosmetic process for treating keratin materials using this composition.

Finally, the invention relates to the use of such a composition for washing keratin materials.

It is common practice to use detergent cosmetic compositions such as shampoos and shower gels, based essentially on surfactants, for washing keratin materials especially such as the hair and the skin. These compositions are applied to the keratin materials, which are preferably wet, and the lather generated by massaging or rubbing with the hands or a toiletry flannel makes it possible, after rinsing with water, to remove the diverse types of soiling initially present on the hair or the skin.

These compositions contain substantial contents of "detergent" surfactants, which, in order to be able to formulate cosmetic compositions with good washing power, must especially give them good foaming power.

The surfactants that are useful for this purpose are generally of anionic, nonionic and/or amphoteric type, and particularly of anionic type.

The products for washing keratin materials that are the most common on the market often contain anionic surfactants of sulfate type, which, although being very good detergent surfactants, are unfriendly to the materials to be washed. In particular, they may have a desiccating effect on keratin materials, and degrade the conditioning of the hair.

Sulfate surfactants are also known to be liable to give rise, in the case of certain sensitive consumers, to tolerance problems, especially on the skin and the eyes.

There is thus a need to offer consumers cosmetic compositions that have good detergent power and especially good foaming power, while at the same time being free of sulfate surfactants as much as possible.

Now, it turns out that the shampoos free of sulfate anionic surfactants that are present on the market generally need, in order to obtain the foam abundance and quality desired by consumers, to contain large amounts of other surfactants.

However, the use of large amounts of these surfactants is undesirable, since it increases the cost of the compositions and may also lead to tolerance problems in the case of the most sensitive consumers.

Thus, there is a real need to provide cosmetic compositions that have satisfactory foaming properties, at least equivalent to those of the prior art, without having to use large amounts of surfactants.

These compositions must also have good detergent properties, have good tolerance especially with respect to the skin, mucous membranes, the scalp and the eyes, and lead to good conditioning of keratin materials.

The Applicant has now discovered that a cosmetic composition containing a particular combination of two anionic surfactants, one of which is of carboxylate type and the other of acylisethionate type, makes it possible to achieve the objectives outlined above.

The subject of the invention is thus a cosmetic composition comprising:
one or more anionic surfactants of carboxylate type, chosen from the compounds of formula (I):

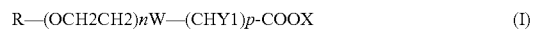

$$R-(OCH_2CH_2)_nW-(CHY1)_p-COOX \qquad (I)$$

with
Y1 denoting a hydrogen atom or a group $(CH_2)_qCOOX$ or a hydroxyl group;
W denoting an oxygen atom, a group $(O\text{-}Glu\text{-}O)_r\text{-}(COCH(Y2)\text{-}(C(OH)COOX)_t)_s$ or a group $CO-NR1$;
Y2 denoting a hydrogen atom or a hydroxyl group;
R1 denoting a hydrogen atom or a methyl group;
X denoting a hydrogen atom, an ammonium ion, an ion derived from an alkali metal or an alkaline-earth metal or an ion derived from an organic amine;
R denoting a linear or branched, preferably linear, alkyl group comprising from 7 to 29 carbon atoms, preferably from 9 to 21 carbon atoms and better still from 11 to 17 carbon atoms, and more preferentially R denotes a linear alkyl group comprising 11 carbon atoms;
Glu denoting a divalent radical derived from glucopyranose with removal of two hydroxyl groups;
p being equal to 0 or 1;
q being an integer ranging from 1 to 10;
n being an integer ranging from 0 to 50;
r denoting a number ranging from 1 to 10;
s being equal to 0 or 1;
t being equal to 0 or 1,
in a content of greater than or equal to 3% by weight relative to the total weight of the composition, and
one or more anionic surfactants of (C8-C22) acylisethionate type, in a content ranging from 2.5% to 8% by weight relative to the total weight of the composition.

The composition according to the invention makes it possible to obtain an abundant foam of very good quality. It especially provides a homogeneous foam which has good persistence over time.

Furthermore, the foam formed from the composition according to the invention spreads easily and uniformly on keratin materials.

For an amount of non-sulfate surfactants that is otherwise equal, the composition according to the invention has better foaming qualities than those of the compositions of the prior art. In other words, the present invention makes it possible to obtain optimum foaming performance when compared with the amount of non-sulfate surfactants present in the composition.

Thus, the present invention makes it possible to formulate compositions which, for a surfactant content equivalent to that of the compositions of the prior art, have superior foaming performance. Above all, the present invention makes it possible to formulate compositions that may contain smaller amounts of surfactants than the compositions of the prior art, while at the same time having at least equivalent or even superior foaming performance.

In addition, the composition according to the invention has good cosmetic properties, and especially affords good conditioning of keratin materials and especially of keratin fibres such as the hair, including when these fibres are sensitized.

Other subjects, characteristics, aspects and advantages of the invention will emerge even more clearly on reading the description and the example that follow.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

The composition according to the invention comprises one or more anionic surfactants of carboxylate type.

For the purposes of the present invention, the term "anionic surfactant of carboxylate type" means an anionic surfactant comprising one or more carboxylic or carboxylate functions (—COOH or —COO$^-$), and not comprising any sulfonate functions (—SO$_3$H or —SO$_3^-$).

The anionic surfactants of carboxylate type are chosen from the compounds of formula (I):

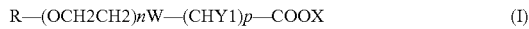

R—(OCH2CH2)$n$W—(CHY1)$p$—COOX     (I)

with

Y1 denoting a hydrogen atom or a group (CH2)qCOOX or a hydroxyl group;

W denoting an oxygen atom, a group (O-Glu-O)r-(COCH(Y2)-(C(OH)COOX)t)s or a group CO—NR1;

Y2 denoting a hydrogen atom or a hydroxyl group;

R1 denoting a hydrogen atom or a methyl group;

X denoting a hydrogen atom, an ammonium ion, an ion derived from an alkali metal or an alkaline-earth metal or an ion derived from an organic amine;

R denoting a linear or branched, preferably linear, alkyl group comprising from 7 to 29 carbon atoms, preferably from 9 to 21 carbon atoms and better still from 11 to 17 carbon atoms, and more preferentially R denotes a linear alkyl group comprising 11 carbon atoms;

Glu denoting a divalent radical derived from glucopyranose with removal of two hydroxyl groups;

p being equal to 0 or 1;

q being an integer ranging from 1 to 10;

n being an integer ranging from 0 to 50;

r denoting a number ranging from 1 to 10;

s being equal to 0 or 1;

t being equal to 0 or 1.

Preferably, the surfactants are chosen from the compounds of formula (I) for which:

n=0, p=1, Y1=H, W=CONH (acylglycinates);
n=0, p=1, W=CON(CH3) and Y1=H (sarcosinates);
n=0, p=1, W=CONH and Y1=CH2CH2COOX (acylglutamates);
n=1 to 50, p=1, Y1=H, W=oxygen atom (alkyl ether carboxylates);
n=0, p=1, s=0, r=1 to 10, Y1=H, W=O-Glu-O (alkyl glucose carboxylates);
n=0, p=1, Y1=OH, t=0, s=1, Y2=OH, r=1 to 10 (alkyl glucoside tartrates);
n=0, p=1, Y1=H, s=1, t=1, Y2=H, r=1 to 10 (alkyl glucoside citrates).

More preferentially, the surfactants are chosen from the compounds of formula (I) for which n=0, p=1 and W=CONR1.

These surfactants may be used in salified or non-salified form.

Salts that may be used in particular include alkali metal salts such as sodium or potassium salts, ammonium salts, amine salts, amino alcohol salts or alkaline-earth metal salts, for example magnesium salts.

Amino alcohol salts that may be mentioned include monoethanolamine, diethanolamine and triethanolamine salts, mono isopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants of carboxylate type are chosen from (C8-C30)acylglutamates and in particular stearoylglutamates, lauroylglutamates and cocoylglutamates; (C8-C30)acylsarcosinates and in particular palmitoylsarcosinates, stearoylsarcosinates, lauroylsarcosinates and cocoylsarcosinates; alkyl ether carboxylates and in particular lauryl ether carboxylates; and mixtures thereof; in particular in the form of alkali metal, alkaline-earth metal, ammonium, amine or amino alcohol salts.

According to a particularly preferred embodiment of the invention, the anionic surfactants of carboxylate type are chosen from (C8-C22)acylsarcosinates, corresponding to formula (IA) below:

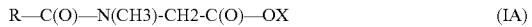

R—C(O)—N(CH3)-CH2-C(O)—OX     (IA)

with

X denoting a hydrogen atom, an ammonium ion, an ion derived from an alkali metal or an alkaline-earth metal or an ion derived from an organic amine; and R denoting a linear or branched, preferably linear, alkyl group comprising from 7 to 21 carbon atoms and preferably from 9 to 17 carbon atoms, and more preferentially R denotes a linear alkyl group comprising 11 carbon atoms.

The lauroylsarcosinates, for example sodium lauroylsarcosinate, are particularly preferred carboxylic anionic surfactants.

Preferably, the composition according to the invention has a content of anionic surfactant(s) of carboxylate type of formula (I) ranging from 3% to 15% by weight, better still from 3.1% to 12% by weight and even better still from 3.2% to 8% by weight, relative to its total weight.

The composition according to the invention also comprises one or more anionic surfactants of (C8-C22)acylisethionate type.

The corresponding surfactants correspond to formula (II) below:

R$^1$COO—R$^2$—SO$_3$M     (II)

with

R$^1$ denoting a linear or branched, preferably linear, alkyl group, comprising from 7 to 21 carbon atoms and preferably from 9 to 17 carbon atoms;

R$^2$ denoting a linear or branched alkylene group, comprising from 2 to 4 carbon atoms and preferably 2 or 3 carbon atoms; and M denoting a hydrogen atom, an ammonium ion, an ion derived from an alkali metal or an alkaline-earth metal or an ion derived from an organic amine.

Preferably, R$^1$ denotes a linear alkyl group comprising from 9 to 17 carbon atoms and preferably from 11 to 15 carbon atoms.

The anionic surfactants of (C8-C22)acylisethionate type are preferably used in the form of salts, and more preferentially in the form of alkali metal or alkaline-earth metal salts, and in particular sodium or magnesium salts.

As examples of surfactants of (C8-C22)acylisethionate type that are particularly preferred, mention may be made especially of cocoyl isethionates and lauroyl methyl isethionates, in particular in the form of sodium salts.

The surfactants of (C8-C22) acylisethionate type are generally prepared by reacting an isethionic acid salt with the C8-C22 fatty acid(s) corresponding to the desired acyl groups.

Depending on the preparation process used, the product obtained is generally in the form of a mixture which may contain variable amounts of residual fatty acid, which may be up to 40% by weight relative to the total weight of the mixture.

As mentioned above, the composition according to the invention contains from 2.5% to 8% by weight of surfactant(s) of (C8-C22)acylisethionate type.

This content is expressed relative to the amount of (C8-C22)acylisethionate compound per se. In particular, the amount of residual fatty acid that may be present in the starting material used is not taken into account.

More preferably, the composition according to the invention has a content of anionic surfactant(s) of (C8-C22) acylisethionate type ranging from 2.8% to 7.5% by weight and better still from 3% to 7% by weight relative to its total weight.

According to a preferred embodiment, the composition according to the present invention presents a weight ratio between the amount of surfactant(s) of carboxylate type of formula (I) and the amount of surfactant(s) of (C8-C22) acylisethionate type ranging from 0.5 to 2, preferably from 0.6 to 1.7, and better still from 0.7 to 1.5.

According to a preferred embodiment, the composition according to the invention has a total content of surfactant(s) of carboxylate type of formula (I) greater than its total content of surfactant(s) of (C8-C22)acylisethionate type.

Also preferably, the composition according to the invention is free of anionic surfactant of sulfate type.

For the purposes of the present invention, the term "anionic surfactant of sulfate type" means surfactants comprising at least one anionic group or group that can be ionized into an anionic group, chosen from sulfate functions (—$OSO_3H$ or —$OSO_3^-$).

Thus, the following anionic surfactants are preferably not present in the composition according to the invention: salts of alkyl sulfates, of alkylamide sulfates, of alkyl ether sulfates, of alkylamido ether sulfates, of alkylaryl ether sulfates, of monoglyceride sulfates.

For the purposes of the present invention, the term "free of" refers to a composition which does not contain (0%) these anionic surfactants of sulfate type or which contains less than 0.1% by weight of such surfactants, relative to the total weight of the composition.

The composition according to the invention may also comprise additional surfactants, other than those mentioned previously, and in particular sulfonate surfactants other than isethionates, one or more amphoteric or zwitterionic surfactants and/or one or more nonionic surfactants.

Thus, the composition according to the invention may comprise one or more additional sulfonate anionic surfactants.

These additional sulfonate surfactants may be chosen from alkyl sulfoacetates, monoalkyl or dialkyl sulfosuccinates, monoalkyl or dialkyl ether sulfosuccinates, monoalkylamido or dialkylamido(ether) sulfosuccinates, acyl N-methyltaurates and α-olefin sulfonates.

When they are present, the amount of the additional sulfonate surfactant(s) preferably ranges from 0.05% to 15% by weight, more preferentially from 0.5% to 10% by weight and better still from 1% to 5% by weight relative to the total weight of the composition.

Thus, the composition according to the invention may comprise one or more amphoteric or zwitterionic surfactants.

The amphoteric or zwitterionic surfactant(s), which are preferably non-silicone, which can be used in the composition according to the present invention may especially be derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of ($C_8$-$C_{20}$)alkylbetaines, ($C_8$-$C_{20}$)alkylsulfobetaines, ($C_8$-$C_{20}$)alkylamido($C_3$-$C_8$)alkylbetaines and ($C_8$-$C_{20}$)alkylamido($C_6$-$C_8$)alkylsulfobetaines.

Among the derivatives of optionally quaternized secondary or tertiary aliphatic amines that may be used, as defined above, mention may also be made of the compounds of respective structures (IIIa) and (IIIb) below:

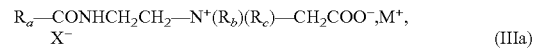

$R_a$—CONHCH$_2$CH$_2$—N$^+$(R$_b$)(R$_c$)—CH$_2$COO$^-$,M$^+$, $\quad$ (IIIa)
$\quad$ X$^-$ in which formula:
  $R_a$ represents a $C_{10}$-$C_{30}$ alkyl or alkenyl group derived from an acid $R_a$COOH preferably present in hydrolysed coconut oil, or a heptyl, nonyl or undecyl group;
  $R_b$ represents a beta-hydroxyethyl group; and
  $R_c$ represents a carboxymethyl group;
  M$^+$ represents a cationic counterion derived from an alkali metal or alkaline-earth metal, such as sodium, an ammonium ion or an ion derived from an organic amine, and
  X$^-$ represents an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate; or alternatively M$^+$ and X$^-$ are absent;

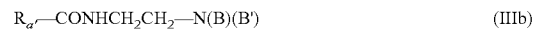

$R_a'$—CONHCH$_2$CH$_2$—N(B)(B') $\quad$ (IIIb)

in which formula:
  B represents the group —CH$_2$CH$_2$OX';
  B' represents the group —(CH$_2$)$_z$Y', with z=1 or 2;
  X' represents the group —CH$_2$COOH, —CH$_2$—COOZ', —CH$_2$CH$_2$COOH, —CH$_2$CH$_2$—COOZ', or a hydrogen atom;
  Y' represents the group —COOH, —COOZ', —CH$_2$CH(OH)SO$_3$H or the group CH$_2$CH(OH)SO$_3$—Z';
  Z' represents a cationic counterion derived from an alkali metal or alkaline-earth metal, such as sodium, an ammonium ion or an ion derived from an organic amine;
  $R_a'$ represents a $C_{10}$-$C_{30}$ alkyl or alkenyl group of an acid $R_a'$—COOH which is preferably present in coconut oil or in hydrolysed linseed oil, or an alkyl group, especially a $C_{17}$ group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid, cocoamphodipropionic acid.

By way of example, mention may be made of the cocoamphodiacetate sold by the company Rhodia under the trade name Miranol® C2M Concentrate.

Use may also be made of the compounds of formula (IIIc):

$$R_{a''}—NHCH(Y'')—(CH_2)_nCONH(CH_2)_{n'}—N(R_d)(R_e) \quad (IIIc)$$

in which formula:
- Y'' represents the group —COOH, —COOZ'', $CH_2CH(OH)SO_3H$ or the group $CH_2CH(OH)SO_3—Z''$;
- $R_d$ and $R_e$ represent, independently of each other, a $C_1$-$C_4$ alkyl or hydroxyalkyl radical;
- Z'' represents a cationic counterion derived from an alkali metal or alkaline-earth metal, such as sodium, an ammonium ion or an ion derived from an organic amine;
- $R_{a''}$ represents a $C_{10}$-$C_{30}$ alkyl or alkenyl group of an acid $R_{a''}$—COOH which is preferably present in coconut oil or in hydrolysed linseed oil;
- n and n' denote, independently of each other, an integer ranging from 1 to 3.

Among the compounds of formula (IIIc), mention may be made of the compound classified in the CTFA dictionary under the name sodium diethylaminopropyl cocoaspartamide and sold by the company Chimex under the name Chimexane HB.

These compounds may be used alone or as mixtures.

Among the amphoteric or zwitterionic surfactants mentioned above, use is preferably made of ($C_8$-$C_{20}$)alkylbetaines such as cocoylbetaine, ($C_8$-$C_{20}$)alkylamido($C_3$-$C_8$)alkylbetaines such as cocamidopropylbetaine, and mixtures thereof, and the compounds of formula (IIIc) such as the sodium salt of diethylaminopropyl laurylaminosuccinamate (INCI name: sodium diethylaminopropyl cocoaspartamide).

In a preferred variant of the invention, the composition contains one or more amphoteric or zwitterionic surfactant(s), preferably chosen from ($C_8$-$C_{20}$)alkylbetaines and ($C_8$-$C_{20}$)alkylamido($C_3$-$C_8$)alkylbetaines, and mixtures thereof.

When they are present, the amount of the amphoteric or zwitterionic surfactant(s) preferably ranges from 0.05% to 15% by weight, more preferentially from 0.5% to 10% by weight and better still from 1% to 8% by weight relative to the total weight of the composition.

Examples of nonionic surfactants that may be used in the compositions of the present invention are described, for example, in the *Handbook of Surfactants* by M. R. Porter, published by Blackie & Son (Glasgow and London), 1991, pp. 116-178. They are especially chosen from fatty alcohols, fatty α-diols, fatty ($C_{1-20}$)alkylphenols and fatty acids, these compounds being polyethoxylated, polypropoxylated or polyglycerolated and containing at least one fatty chain comprising, for example, from 8 to 18 carbon atoms, the number of ethylene oxide or propylene oxide groups possibly ranging especially from 1 to 100, and the number of glycerol groups possibly ranging especially from 1 to 30.

Mention may also be made of condensates of ethylene oxide and of propylene oxide with fatty alcohols; polyethoxylated fatty amides preferably having from 1 to 30 ethylene oxide units, polyglycerolated fatty amides comprising on average 1 to 5, and in particular 1.5 to 4, glycerol groups, ethoxylated fatty acid esters of sorbitan containing from 2 to 30 ethylene oxide units, fatty acid esters of sucrose, fatty acid esters of polyethylene glycol, ($C_{6-24}$ alkyl)polyglycosides, N—($C_{6-24}$ alkyl)glucamine derivatives, amine oxides such as ($C_{10-14}$)alkylamine oxides or N($C_{10-14}$ acyl)aminopropylmorpholine oxides.

Among nonionic surfactants, the use of alkyl(poly)glycoside nonionic surfactants is more particularly preferred.

The term "alkyl(poly)glycoside" denotes an alkylpolyglycoside or an alkylmonoglycoside, also referred to in the present patent application as an alkylglycoside, which may be alkoxylated with one or more alkylene oxide groups, preferentially of $C_2$-$C_4$.

The alkyl(poly)glycoside nonionic surfactant(s) used, alone or as mixtures, in accordance with the present invention may be represented by formula (IV) below:

$$R_1O—(R_2O)_t(G)_v \quad (IV)$$

in which:
- $R_1$ represents a saturated or unsaturated, linear or branched alkyl group comprising from 8 to 24 carbon atoms, or an alkylphenyl group in which the linear or branched alkyl group comprises from 8 to 24 carbon atoms,
- $R_2$ represents an alkylene group comprising from about 2 to 4 carbon atoms,
- G represents a saccharide unit comprising from 5 to 6 carbon atoms,
- t denotes a value ranging from 0 to 10 and preferably from 0 to 4, and
- v denotes a value ranging from 1 to 15.

Preferably, the alkyl(poly)glycoside nonionic surfactant(s) correspond to formula (IV) in which:
- $R_1$ denotes a linear or branched, saturated or unsaturated alkyl group comprising from 8 to 18 carbon atoms,
- G denotes glucose, fructose or galactose, preferably glucose,
- t denotes a value ranging from 0 to 3, and is preferably equal to 0,
- and $R_2$ and v are as defined previously.

The degree of polymerization of the alkyl(poly)glycoside nonionic surfactant(s) as represented, for example, by the index v in formula (IV) above ranges on average from 1 to 15 and preferably from 1 to 4. This degree of polymerization more particularly ranges from 1 to 2 and better still from 1.1 to 1.5, on average.

The glycoside bonds between the saccharide units are of 1-6 or 1-4 type and preferably of 1-4 type.

The alkyl(poly)glycoside nonionic surfactants that may be used in the present invention are preferably alkyl(poly)glucosides, especially represented by the products sold by the company Cognis under the names Plantaren® (600 CS/U, 1200 and 2000) or Plantacare® (818, 1200 and 2000). Use may also be made of the products sold by the company SEPPIC under the names Triton CG 110 (or Oramix CG 110) and Triton CG 312 (or Oramix® NS 10), the products sold by the company BASF under the name Lutensol GD 70, or those sold by the company Chem Y under the name AG10 LK.

As nonionic surfactant cocoyl glucoside, i.e. a mixture of ($C_8$-$C_{16}$)alkyl polyglucosides such as the product sold under the name Plantacare 818UP by the company BASF, may be most particularly used.

When they are present, the amount of the nonionic surfactant(s) preferably ranges from 0.1% to 10% by weight and better still from 0.5% to 5% by weight relative to the total weight of the composition.

Preferably, the total amount of surfactants in the composition according to the invention ranges from 5.5% to 30% by weight relative to the total weight of the composition.

More preferentially, this total amount is less than or equal to 21% by weight, relative to the total weight of the composition, and may preferably be between 5.5% and 21% by weight, especially between 7% and 20% by weight, or even between 10% and 19.5% by weight, relative to the total weight of the composition.

The composition according to the invention may also comprise one or more cationic polymers.

The term "cationic polymer" means any polymer containing cationic groups and/or groups that can be ionized to cationic groups, which are preferably non-siliceous.

The cationic polymers that may be used in accordance with the present invention may be chosen from any of those already known per se for styling the hair, namely, especially, those described in patent application EP-A-0 337 354 and in French patent applications FR-A-2 270 846, 2 383 660, 2 598 611, 2 470 596 and 2 519 863.

The preferred cationic polymers that may be used in the composition according to the invention are chosen from those containing units comprising primary, secondary, tertiary and/or quaternary amine groups that may either form part of the main polymer chain or may be borne by a side substituent directly connected thereto.

The cationic polymers preferably have a weight-average molecular mass of greater than $10^5$, preferably greater than $10^6$ and more preferably of between $10^6$ and $10^8$.

Among the cationic polymers that may be used in accordance with the invention, mention may be made more particularly of polymers of polyamine, polyaminoamide and polyquaternary ammonium type.

The polymers of polyamine, polyaminoamide and polyquaternary ammonium type that may be used in the composition according to the present invention are especially those described in French patents 2 505 348 and 2 542 997.

Among these polymers, mention may be made especially of:

(1) homopolymers or copolymers derived from acrylic or methacrylic esters or amides and comprising at least one of the units of formulae (V), (VI), (VII) and (VIII) below:

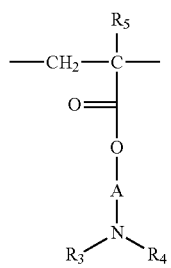

(V)

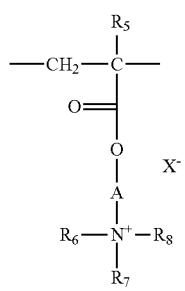

(VI)

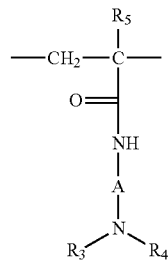

(VII)

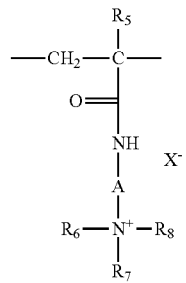

(VIII)

in which:
$R_3$ and $R_4$, which may be identical or different, represent a hydrogen atom or an alkyl group containing from 1 to 6 carbon atoms, and preferably a methyl or ethyl group,
$R_5$, which may be identical or different, denote a hydrogen atom or a $CH_3$ group,
A, which may be identical or different, represent a linear or branched alkyl group of 1 to 6 carbon atoms, preferably 2 or 3 carbon atoms, or a hydroxyalkyl group comprising 1 to 4 carbon atoms,
$R_6$, $R_7$ and $R_8$, which may be identical or different, represent an alkyl group containing from 1 to 18 carbon atoms or a benzyl group, and preferably an alkyl group containing from 1 to 6 carbon atoms,
$X^-$ denotes an anion derived from a mineral or organic acid, preferably a methosulfate anion or a halide, and better still a chloride or bromide.

The copolymers of family (1) may also contain one or more units derived from comonomers which may be chosen from the family of acrylamides, methacrylamides, diacetone acrylamides, acrylamides and methacrylamides substituted on the nitrogen atom with lower ($C_1$-$C_4$) alkyls, acrylic or methacrylic acids or esters thereof, vinyllactams such as vinylpyrrolidone or vinylcaprolactam, and vinyl esters.

Thus, among these copolymers of the family (1), mention may be made of:
copolymers of acrylamide and of dimethylaminoethyl methacrylate quaternized with dimethyl sulfate or with a dimethyl halide, such as the product sold under the name Hercofloc by the company Hercules,
copolymers of acrylamide and of methacryloyloxyethyltrimethylammonium chloride, described, for example, in patent application EP-A-080 976 and sold under the name Bina Quat P 100 by Ciba-Geigy,
the copolymer of acrylamide and of methacryloyloxyethyltrimethylammonium methosulfate sold under the name Reten by the company Hercules,
quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755, or alternatively the products known as Copolymer 845, 958 and 937. These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, quaternized vinylpyrrolidone/dimethylaminopropylmethacrylamide copolymers such as the product sold under the name Gafquat HS 100 by the company ISP, and crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide. Use may be made more particularly of a crosslinked acrylamide/methacryloyloxyethyltrimethylammonium chloride copolymer (20/80 by weight) in the form of a dispersion containing 50% by weight of the said copolymer in mineral oil. This dispersion is sold under the name Salcare® SC 92 by the company Ciba. Use may also be made of a crosslinked methacryloyloxyethyltrimethylammonium chloride homopolymer (INCI name Polyquaternium-37), for example the polymer sold under the name Cosmedia Ultragel 300 by the company Cognis; or as a dispersion in mineral oil or in a liquid ester; these dispersions are sold under the names Salcare® SC 95 and Salcare® SC 96 by the company Ciba.

(2) polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers. Such polymers are especially described in French patents 2 162 025 and 2 280 361.

(3) water-soluble polyamino amides prepared in particular by polycondensation of an acidic compound with a polyamine. These polyaminoamides may be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyaminoamide. These polyaminoamides can be alkylated or, if they comprise one or more tertiary amine functions, they can be quaternized. Such polymers are especially described in French patents 2 252 840 and 2 368 508.

(4) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl group comprises from 1 to 4 carbon atoms and preferably denotes methyl, ethyl or propyl. Such polymers are especially described in French patent 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(5) The polymers obtained by reaction of a polyalkylene polyamine comprising two primary amine groups and at least one secondary amine group with a dicarboxylic acid chosen from diglycolic acid and saturated aliphatic dicarboxylic acids having from 3 to 8 carbon atoms. The mole ratio between the polyalkylene polyamine and the dicarboxylic acid is between 0.8:1 and 1.4:1; the polyamino amide resulting therefrom is reacted with epichlorohydrin in a mole ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl-diethylenetriamine copolymer.

(6) Cyclopolymers of alkyldiallylamine or of dialkyldiallylammonium, such as the homopolymers or copolymers comprising, as main constituent of the chain, units corresponding to formula (IX) or (X):

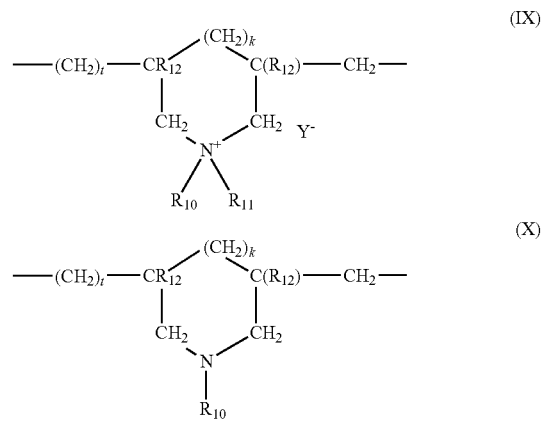

in which k and t are equal to 0 or 1, the sum k+t being equal to 1; $R_{12}$ denotes a hydrogen atom or a methyl group; $R_{10}$ and $R_{11}$, independently of each other, denote an alkyl group containing from 1 to 6 carbon atoms, a hydroxyalkyl group in which the alkyl group preferably contains 1 to 5 carbon atoms, a lower ($C_1$-$C_4$) amidoalkyl group, or $R_{10}$ and $R_{11}$ may denote, together with the nitrogen atom to which they are attached, heterocyclic groups such as piperidyl or morpholinyl; $Y^-$ is an anion such as bromide, chloride, acetate, borate, citrate, tartrate, bisulfate, bisulfite, sulfate or phosphate. These polymers are in particular described in French patent 2 080 759 and in its Certificate of Addition 2 190 406.

$R_{10}$ and $R_{11}$, independently of each other, preferably denote an alkyl group having from 1 to 4 carbon atoms.

Among the polymers defined above, mention may be made more particularly of the dimethyldiallylammonium chloride homopolymer sold under the name Merquat 100 by the company Nalco and its homologues of low weight-average molecular weights, and the copolymers of diallyldimethylammonium chloride and of acrylamide sold under the name Merquat 550.

(7) The quaternary diammonium polymer in particular containing repeating units corresponding to the formula (XI):

in which:

$R_{13}$, $R_{14}$, $R_{15}$ and Rib, which may be identical or different, represent aliphatic, alicyclic or arylaliphatic groups containing from 1 to 20 carbon atoms or lower hydroxyalkylaliphatic radicals, or alternatively $R_{13}$, $R_{14}$, $R_{15}$ and Rib, together or separately, constitute, with the nitrogen atoms to which they are attached, heterocycles optionally containing a second heteroatom other than nitrogen, or alternatively $R_{13}$, $R_{14}$, $R_{15}$ and Rib represent a linear or branched $C_1$-$C_6$ alkyl group substituted with a nitrile, ester, acyl or amide group or a group $COOR_{17}D$ or $CONHR_{17}D$ where $R_{17}$ is an alkylene and D is a quaternary ammonium group, $A_1$ and $B_1$ represent polymethylene groups containing from 2 to 20 carbon atoms which may be linear or branched, and saturated or unsaturated, and which may contain, linked to or inserted in the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid, $A_1$, $R_{13}$ and $R_{15}$ can form, with the two nitrogen atoms to which they are attached, a piperazine ring. In addition, if $A_1$ denotes a linear or branched, saturated or unsaturated alkylene or hydroxyalkylene radical, $B_1$ may also denote a group $(CH_2)_n$—CO-D-OC—$(CH_2)_p$—, n and p are integers ranging from 2 to 20 approximately, in which D denotes:

a) a glycol residue of formula: —O—Z—O—, where Z denotes a linear or branched hydrocarbon-based radical or a group corresponding to one of the following formulae:

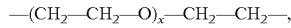

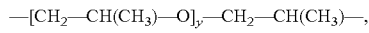

in which x and y denote an integer from 1 to 4, representing a defined and unique degree of polymerization or any number from 1 to 4 representing an average degree of polymerization, b) a bis-secondary diamine residue such as a piperazine derivative, c) a bis-primary diamine residue of formula: —NH—Y—NH—, where Y denotes a linear or branched hydrocarbon-based radical, or else the divalent radical —CH$_2$—CH$_2$—S—S—CH$_2$—CH$_2$—, d) a ureylene group of formula —NH—CO—NH—.

Preferably, $X^-$ is an anion such as chloride or bromide.

These polymers have a number-average molecular mass generally of between 1000 and 100 000.

Polymers of this type are especially described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of polymers that are formed from repeating units corresponding to formula (XII):

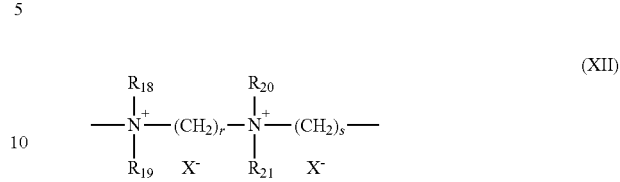

in which $R_{18}$, $R_{19}$, $R_{20}$ and $R_{21}$, which may be identical or different, denote an alkyl or hydroxyalkyl group containing from 1 to 4 carbon atoms approximately, r and s are integers ranging from 2 to 20 approximately, and $X^-$ is an anion derived from a mineral or organic acid.

A compound of formula (XII) that is particularly preferred is that for which $R_{18}$, $R_{19}$, $R_{20}$ and $R_{21}$ represent a methyl radical and r=3, s=6 and X=Cl, called hexadimethrine chloride in INCI nomenclature (CTFA).

(8) Polyquaternary ammonium polymers formed especially from units of formula (XIII):

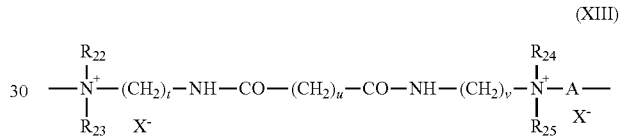

in which:

$R_{22}$, $R_{23}$, $R_{24}$ and $R_{25}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH group, where p is equal to 0 or to an integer between 1 and 6, with the proviso that $R_{22}$, $R_{23}$, $R_{24}$ and $R_{25}$ do not simultaneously represent a hydrogen atom, t and u, which may be identical or different, are integers between 1 and 6, v is equal to 0 or to an integer between 1 and 34, $X^-$ denotes an anion such as a halide, A denotes a dihalide radical or preferably represents —CH$_2$—CH$_2$—O—CH$_2$—CH$_2$—.

Such compounds are especially described in patent application EP-A-122 324.

Among these, mention may be made, for example, of the products Mirapol® A 15, Mirapol® AD1, Mirapol® AZ1 and Mirapol® 175, sold by the company Miranol.

(9) Quaternary polymers of vinylpyrrolidone and/or of vinylimidazole, for instance the products sold under the names Luviquat® FC 905, FC 550 and FC 370 and Luviquat Excellence by the company BASF.

(10) Cationic polysaccharides, preferably cationic celluloses and galactomannan gums.

Among cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are described in French patent 1 492 597. These polymers are also defined in the CTFA dictionary as quaternary ammoniums of hydroxyethylcellulose that have reacted with an epoxide substituted with a trimethylammonium group.

The cationic cellulose copolymers or the cellulose derivatives grafted with a water-soluble quaternary ammonium monomer are described especially in U.S. Pat. No. 4,131,576, such as hydroxyalkyl celluloses, for instance hydroxymethyl, hydroxyethyl or hydroxypropyl celluloses grafted especially with a methacryloylethyltrimethylammonium, methacrylamidopropyltrimethylammonium or dimethyldiallylammonium salt.

A cationic cellulose copolymer that may especially be mentioned is Polyquaternium-4, which is a copolymer of hydroxyethylcellulose and of diallyldimethylammonium chloride.

Mention may also be made of associative celluloses such as alkylhydroxyethylcelluloses quaternized with C8-C30 fatty chains, such as the product Quatrisoft LM 200®, sold by the company Amerchol/Dow Chemical (INCI name Polyquaternium-24) and the products Crodacel QM® (INCI name PG-Hydroxyethylcellulose cocodimonium chloride), Crodacel QL® (C12 alkyl) (INCI name PG-Hydroxyethylcellulose lauryldimonium chloride) and Crodacel QS@ (C18 alkyl) (INCI name PG-Hydroxyethylcellulose stearyldimonium chloride) sold by the company Croda.

Mention may also be made of other fatty-chain hydroxyethylcellulose derivatives such as the commercial products Softcat Polymer SL® such as SL-100, SL-60, SL-30 and SL-5 from the company Amerchol/Dow chemical of INCI name Polyquaternium-67.

The cationic galactomannan gums are described more particularly in U.S. Pat. Nos. 3,589,578 and 4,031,307, in particular guar gums containing cationic trialkylammonium groups. Guar gums modified with a salt such as 2,3-epoxypropyltrimethylammonium chloride are used, for example.

Among this family of cationic polymers, the fatty-chain hydroxyethylcellulose derivative of INCI name Polyquaternium-67 is particularly preferred.

(11) Cationic proteins or cationic protein hydrolysates, polyalkyleneimines, in particular polyethyleneimines, polymers containing vinylpyridine or vinylpyridinium units, condensates of polyamines and of epichlorohydrin, quaternary polyureylenes and chitin derivatives.

The cationic proteins or protein hydrolysates are, in particular, chemically modified polypeptides bearing quaternary ammonium groups at the end of the chain, or grafted thereon. Their molecular mass may vary, for example, from 1500 to 10 000 and in particular from 2000 to 5000 approximately. Among these compounds, mention may be made especially of:

collagen hydrolysates bearing triethylammonium groups, such as the products sold under the name Quat-Pro E by the company Maybrook and referred to in the CTFA dictionary as Triethonium Hydrolyzed Collagen Ethosulfate, collagen hydrolysates bearing trimethylammonium chloride and trimethylstearylammonium chloride groups, which are sold under the name Quat-Pro S by the company Maybrook and are referred to in the CTFA dictionary as Stearthrimonium Hydrolyzed Collagen, animal protein hydrolysates bearing trimethylbenzylammonium groups, such as the products sold under the name Crotein BTA by the company Croda and referred to in the CTFA dictionary as Benzyltrimonium hydrolyzed animal protein, protein hydrolysates bearing quaternary ammonium groups on the polypeptide chain, the said ammonium groups comprising at least one alkyl radical having from 1 to 18 carbon atoms.

Among these protein hydrolysates, mention may be made, inter alia, of:

Croquat L, in which the quaternary ammonium groups comprise a C12 alkyl group,

Croquat M, in which the quaternary ammonium groups comprise C10-C18 alkyl groups, Croquat S, in which the quaternary ammonium groups comprise a C18 alkyl group, Crotein Q, in which the quaternary ammonium groups comprise at least one alkyl group having from 1 to 18 carbon atoms.

These various products are sold by the company Croda.

Other quaternized proteins or hydrolysates are, for example, those corresponding to the formula (XIV):

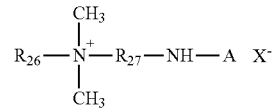

(XIV)

in which X⁻ is an anion of an organic or mineral acid, A denotes a protein residue derived from collagen protein hydrolysates, $R_{26}$ denotes a lipophilic group comprising up to 30 carbon atoms, $R_{27}$ represents an alkylene group having 1 to 6 carbon atoms. Mention may be made, for example, of the products sold by the company Inolex, under the name Lexein QX 3000, referred to in the CTFA dictionary as Cocotrimonium Collagen Hydrolysate.

Mention may also be made of quaternized plant proteins such as wheat, corn or soybean proteins, for instance quaternized wheat proteins. Mention may be made of those sold by the company Croda under the names Hydrotriticum WQ or QM, referred to in the CTFA dictionary as Cocodimonium hydrolysed wheat protein, Hydrotriticum QL, referred to in the CTFA dictionary as Laurdimonium hydrolysed wheat protein, or else Hydrotriticum QS, referred to in the CTFA dictionary as Steardimonium hydrolysed wheat protein.

(12) Polyamines such as Polyquart R H sold by Cognis, referred to under the name polyethylene glycol (15) tallow polyamine in the CTFA dictionary.

(13) Polymers comprising in their structure:
(a) one or more units corresponding to formula (A) below:

(A)

(b) optionally one or more units corresponding to formula (B) below:

(B)

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to formula (A) and from 0 to 95 mol % of units corresponding to formula (B), preferentially from 10 mol % to 100 mol % of units corresponding to formula (A) and from 0 to 90 mol % of units corresponding to formula (B).

These polymers may be obtained, for example, by partial hydrolysis of polyvinylformamide.

This hydrolysis may be performed in an acidic or basic medium.

The weight-average molecular mass of the said polymer, measured by light scattering, may range from 1000 to 3 000 000 g/mol, preferably from 10 000 to 1 000 000 g/mol and more particularly from 100 000 to 500 000 g/mol.

The cationic charge density of these polymers can vary from 2 to 20 meq/g, preferably from 2.5 to 15 meq/g and more particularly from 3.5 to 10 meq/g.

The polymers comprising units of formula (A) and optionally units of formula (B) are sold especially under the name Lupamin by the company BASF, for instance, and in a non-limiting manner, the products sold under the names Lupamin 9095, Lupamin 5095, Lupamin 1095, Lupamin 9030 and Lupamin 9010.

Preferably, the cationic polymer(s) that may be used in the composition according to the invention are chosen from those of families (1), (6), (9) and (10), and more preferentially from those of families (1), (6) and (10), and better still (10).

The cationic polymer(s) that may be used in the composition according to the invention preferably represent, when they are present, from 0.05% to 10% by weight and better still from 0.1% to 3% by weight relative to the total weight of the composition.

The composition according to the invention may also contain one or more silicones.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups, aryl groups, hydroxyl groups and alkoxy groups. Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold especially under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

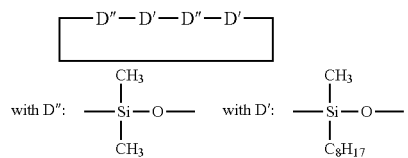

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*.

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C$_1$-C$_{20}$)dialkylsiloxanes.

The silicone gums that may be used in accordance with the invention are in particular polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:

the mixtures formed from a hydroxy-terminated polydimethylsiloxane or dimethiconol (CTFA) chain, and from a cyclic polydimethylsiloxane, also known as cyclomethicone (CTFA), such as the product Q2 1401 sold by the company Dow Corning;

mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, and more particularly of a PDMS gum and of a PDMS oil, such as the product SF 1236 from the company General Electric. The product SF 1236 is a mixture of a gum SE 30 defined above, with a viscosity of 20 m$^2$/s and of an oil SF 96 with a viscosity of $5\times10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$, in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, and which are silicones of dimethyl/trimethylsiloxane structure.

Mention may also be made of resins of the trimethyl siloxysilicate type, sold in particular under the names X22-4914, X21-5034 and X21-5037 by the company Shin-Etsu.

The organomodified silicones that may be used in accordance with the invention are silicones as defined previously and comprising in their structure one or more organofunctional groups attached via a hydrocarbon-based group.

The organomodified silicones may be polydiarylsiloxanes, in particular polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ m$^2$/s at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Mention may also be made, among the organomodified silicones, of polyorganosiloxanes comprising:

substituted or unsubstituted amine groups, such as the products sold under the names GP 4 Silicone Fluid and GP 7100 by the company Genesee or the products sold under the names Q2 8220 and Dow Corning 929 or 939 by the company Dow Corning. The substituted amine groups are, in particular, $C_1$-$C_4$ amino alkyl groups;
alkoxy groups such as the product sold under the name Silicone Copolymer F-755 by SWS Silicones, and Abil Wax® 2428, 2434 and 2440 by the company Goldschmidt.
hydroxyl groups, such as the product sold under the name Belsil DM 3560 VP by the company Wacker.

The preferred silicones are chosen from polydimethylsiloxanes, amino silicones and dimethiconols (silicones bearing hydroxyl groups).

The silicone(s) that may be used in the composition according to the invention preferably represent, when they are present, from 0.05% to 10% by weight and better still from 0.1% to 5% by weight relative to the total weight of the composition.

Preferably, the composition according to the invention is aqueous and comprises at least 30% by weight of water, preferably at least 50% by weight, more preferentially at least 70% by weight and better still at least 80% by weight of water relative to its total weight.

The composition can additionally comprise one or more water-soluble organic solvents (solubility of greater than or equal to 5% by weight in water at 25° C. and at atmospheric pressure).

Mention may be made, as water-soluble organic solvent, for example, of linear or branched and preferably saturated monoalcohols or diols comprising from 2 to 10 carbon atoms, such as ethyl alcohol, isopropyl alcohol, hexylene glycol (2-methyl-2,4-pentanediol), neopentyl glycol, 3-methyl-1,5-pentanediol, butylene glycol, dipropylene glycol or propylene glycol; aromatic alcohols, such as phenylethyl alcohol; polyols comprising more than two hydroxyl functional groups, such as glycerol; polyol ethers, such as, for example, ethylene glycol monomethyl, monoethyl and monobutyl ethers, propylene glycol or its ethers, such as, for example, propylene glycol monomethyl ether; and also diethylene glycol alkyl ethers, in particular $C_1$-$C_4$ alkyl ethers, for instance diethylene glycol monoethyl ether or monobutyl ether, alone or as a mixture.

The water-soluble organic solvents, when they are present, generally represent between 1% and 20% by weight and preferably between 5% and 10% by weight relative to the total weight of the composition.

The composition according to the invention may also comprise one or more additives other than the compounds of the invention.

As additives that may be used in accordance with the invention, mention may be made of anionic, nonionic or amphoteric polymers or mixtures thereof, cationic surfactants, antidandruff agents, anti-seborrhoea agents, agents for preventing hair loss and/or for promoting hair regrowth, fatty substances, vitamins and provitamins including panthenol, sunscreens, mineral or organic pigments, sequestrants, plasticizers, solubilizers, acidifying agents, mineral or organic thickeners, especially polymeric thickeners, opacifiers or nacreous agents, antioxidants, hydroxy acids, fragrances and preserving agents.

Needless to say, a person skilled in the art will take care to select this or these optional additional compound(s) such that the advantageous properties intrinsically associated with the composition according to the invention are not, or are not substantially, adversely affected by the envisaged addition(s).

The above adjuvants may generally be present in an amount, for each of them, of between 0.001% and 20% by weight relative to the total weight of the composition.

The present invention also relates to a cosmetic process for treating keratin materials, which consists in applying to the said materials an effective amount of a composition as described above, optionally working the composition into a lather and then, after an optional leave-on time, removing it by rinsing.

The leave-on time of the composition on the keratin materials may range from a few seconds to 60 minutes, better still from 5 seconds to 30 minutes and even better still from 10 seconds to 10 minutes.

The composition may be applied to wet or dry keratin materials. It is preferably applied to wet keratin materials.

Finally, the present invention relates to the use of a composition as described above for washing keratin materials.

In the present invention, the term "keratin materials" denotes the skin and the scalp, and keratin fibres in particular such as the hair. More preferably, the keratin material is hair.

The examples that follow serve to illustrate the invention without, however, being limiting in nature.

EXAMPLES

In the examples that follow, all the amounts are given as mass percentages of active material relative to the total weight of the composition.

Example 1

The following shampoo compositions were prepared from the ingredients indicated in the table below.

For each of these compositions, the foaming power was determined by proceeding as follows:

An amount of test composition is placed in a mixer, this amount being identical for all the compositions, and is diluted at an identical dilution rate for all the compositions; the mixture is mixed vigorously for 1 minute with a mechanical mixer, at room temperature (25° C.), and is then transferred immediately into a measuring cylinder. The volume of foam generated is then measured. The volume of foam thus obtained for each composition is also indicated in the table below.

| Composition | A | B | C | D | E |
|---|---|---|---|---|---|
| Sodium lauroyl methyl isethionate (2) | — | — | — | — | — |
| Sodium cocoyl isethionate (1) | 5 | 5 | 3.5 | 3 | 3 |
| Sodium lauroyl sarcosinate (3) | 6.5 | 6.5 | 4.5 | 4 | 4 |
| Cocoyl glucoside (4) | 1.5 | 1.5 | 1 | 1.5 | 1.5 |
| Cocoyl betaine (5) | 6 | 6 | 4.5 | 3.6 | 3.6 |
| Carbomer | 0.25 | 0.25 | 0.25 | 0.25 | 0.25 |
| Polyquaternium-10 | 0.52 | 0.52 | 0.52 | 0.88 | 0.88 |
| Glycol distearate | 1.2 | — | 1.2 | 1.2 | 1.2 |
| Polydimethylsiloxane (60 000 cSt) | 1.75 | — | 1.75 | 1.75 | — |
| Sodium chloride | qs | qs | qs | qs | qs |
| Preserving agent, fragrance | qs | qs | qs | qs | qs |
| Water | qs 100% | qs 100% | qs 100% | qs 100% | qs 100% |
| Total surfactant content (weight %) | 19 | 19 | 13.5 | 12.1 | 12.1 |
| Foam volume (ml) | 480 | 500 | 370 | 380 | 480 |

(1) sold under the name Hostapon SCI 85 by the company Clariant
(2) sold under the name Iselux by the company Innospec
(3) sold under the name Oramix L30 by the company SEPPIC
(4) sold under the name Plantacare 818 UP by the company BASF
(5) sold under the name Dehyton AB 30 by the company BASF.

The above results show that the compositions according to the invention have excellent foaming power. The foam is abundant, creamy and soft while at the same time remaining light.

In addition, these compositions proved to have very good detergent power. Hair washed using these compositions is clean and also has a good level of conditioning, especially on dry hair, in particular in terms of sheen and lightness.

Example 2

The following shampoo compositions were prepared from the ingredients indicated in the table below.

For each of these compositions, the foaming power was determined in the same manner as in Example 1.

| Composition | F | G | H |
|---|---|---|---|
| Sodium lauroyl methyl isethionate (1) | 5 | 5.7 | 3.5 |
| Sodium lauroyl sarcosinate (2) | 6.5 | 8 | 4.5 |
| Cocoyl glucoside (3) | 1.5 | 1 | 1 |
| Cocoyl betaine (4) | 6 | 1 | 4.5 |
| Carbomer | 0.25 | 0.25 | 0.25 |
| Polyquaternium-10 | 0.52 | 0.52 | 0.52 |
| Glycol distearate | 1.2 | 1.2 | 1.2 |
| Polydimethylsiloxane (60 000 cSt) | 1.75 | 1.75 | 1.75 |
| Preserving agent, fragrance | qs | qs | qs |
| Water | qs 100% | qs 100% | qs 100% |
| Total surfactant content (weight %) | 19 | 15.7 | 13.5 |
| Foam volume (ml) | 470 | 470 | 370 |

(1) sold under the name Iselux by the company Innospec
(2) sold under the name Oramix L30 by the company SEPPIC
(3) sold under the name Plantacare 818 UP by the company BASF
(4) sold under the name Dehyton AB 30 by the company BASF.

The above results show that the above compositions also have excellent foaming power. The foam is abundant, creamy and soft while at the same time remaining light. In addition, these compositions proved to have very good detergent power. Hair washed using these compositions is clean and also has a good level of conditioning, especially on dry hair, in particular in terms of sheen and lightness.

Example 3

The following shampoo compositions were prepared from the ingredients indicated in the table below.

| Composition | I | J |
|---|---|---|
| Sodium lauroyl methyl isethionate (1) | 3 | — |
| Sodium cocoyl isethionate (5) | — | 3 |
| Sodium lauroyl sarcosinate (2) | 4 | 4 |
| Cocoyl glucoside (3) | 1.5 | 1.5 |
| Cocoyl betaine (4) | 6 | 3.6 |
| Sodium lauryl sulfoacetate (and) disodium laureth sulfosuccinate | — | 2 |
| Carbomer | 0.25 | 0.25 |
| Polyquaternium-10 | 0.52 | 0.52 |
| Glycol distearate | 1.2 | 1.2 |
| Polydimethylsiloxane (60 000 cSt) | 1.75 | 1.75 |
| Preserving agent, fragrance | qs | qs |
| Water | qs 100% | qs 100% |
| Total surfactant content (weight %) | 14.5 | 14.1 |
| Foam volume (ml) | 340 | 380 |

(1) sold under the name Iselux LQ-CLR-SB by the company Innospec
(2) sold under the name Oramix L30 by the company SEPPIC
(3) sold under the name Plantacare 818 UP by the company BASF
(4) sold under the name Dehyton AB 30 by the company BASF
(5) sold under the name Hostapon SCI 85 by the company Clariant.

Example 4

The following shampoo compositions were prepared from the ingredients indicated in the table below.

| Composition | K | L |
|---|---|---|
| Sodium lauroyl methyl isethionate (1) | 4.9 | 6.5 |
| Sodium lauroyl sarcosinate (2) | 3.3 | 5 |
| Cocoyl glucoside (3) | 4.9 | 3 |
| Cocoyl betaine (4) | 4.9 | 2.5 |
| Carbomer | 0.25 | 0.25 |
| Polyquaternium-10 | — | 0.52 |
| Glycol distearate | — | 1.2 |
| Polydimethylsiloxane (60 000 cSt) | — | 1.75 |
| Preserving agent, fragrance | qs | qs |
| Water | qs 100% | qs 100% |
| Total surfactant content (weight %) | 18 | 17 |

These compositions have excellent foaming power. The foam is abundant, creamy and soft while at the same time remaining light. In addition, these compositions proved to have very good detergent power. Hair washed using these compositions is clean and also has a good level of conditioning, especially on dry hair, in particular in terms of sheen and lightness.

The invention claimed is:
1. A cosmetic composition comprising:
at least one anionic surfactant of carboxylate type, chosen from acylsarcosinates corresponding to formula (IA):

R—C(O)—N(CH3)-CH2-C(O)—OX    (IA)

wherein:
X is chosen from a hydrogen atom, an ammonium ion, an ion derived from an alkali metal or an alkaline-earth metal, or an ion derived from an organic amine; and
R is chosen from a linear or branched alkyl group comprising from 9 to 17 carbon atoms,
the anionic surfactant of carboxylate type being present in an amount ranging from about 3% to about 8% by weight, relative to the total weight of the composition,
at least one anionic surfactant of acylisethionate type, chosen from compounds of formula (II):

$R^1$COO—$R^2$—$SO_3$M    (II)

wherein:
$R^1$ is chosen from a linear or branched alkyl group, comprising from 9 to 17 carbon atoms;
$R^2$ is chosen from a linear or branched alkylene group comprising from 2 to 4 carbon atoms; and
M is chosen from a hydrogen atom, an ammonium ion, an ion derived from an alkali metal or an alkaline-earth metal, or an ion derived from an organic amine,
the anionic surfactant of acylisethionate type being present in an amount ranging from about 2.5% to about 8% by weight, relative to the total weight of the composition,
at least one nonionic surfactant, and
at least one cationic polymer,
wherein the weight ratio of the surfactant of carboxylate type and the surfactant of acylisethionate type ranges from 0.6 to 2.
2. The composition according to claim 1, wherein in formula (IA) R is a linear alkyl group comprising 11 carbon atoms.
3. The composition according to claim 1, wherein in formula (II)
$R^1$ is chosen from a linear or branched alkyl group, comprising from 11 to 15 carbon atoms; and
$R^2$ is chosen from a linear or branched alkylene group comprising 2 carbon atoms, or 3 carbon atoms.

4. The composition according to claim 1, wherein the anionic surfactant of acylisethionate type is present in an amount ranging from about 2.8% to about 7.5% by weight, relative to the total weight of the composition.
5. The composition according to claim 1, wherein the at least one acylsarcosinate is present in an amount greater than the amount of surfactant of acylisethionate type.
6. The composition according to claim 1, wherein the composition is free of anionic surfactant of sulfate type.
7. The composition according to claim 1, further comprising at least one additional sulfonate anionic surfactant other than isethionates, chosen from alkyl sulfoacetates, monoalkyl or dialkyl sulfosuccinates, monoalkyl or dialkyl ether sulfosuccinates, monoalkylamido or dialkylamido (ether) sulfosuccinates, acyl N-methyltaurates or α-olefin sulfonates.
8. The composition according to claim 7, wherein the additional sulfonate anionic surfactant is present in an amount ranging from about 0.05% to about 15% by weight, relative to the total weight of the composition.
9. The composition according to claim 1, further comprising at least one additional surfactant chosen from amphoteric or zwitterionic surfactants, (C8-C20) alkylbetaines, (C8-C20)alkylamido(C3-C8)alkylbetaines, or mixtures thereof.
10. The composition according to claim 9, wherein the additional surfactant is present in an amount ranging from about 0.05% to about 15% by weight, relative to the total weight of the composition.
11. The composition according to claim 1, wherein the at least one nonionic surfactant is chosen from compounds of formula (IV):

$R_1$O—$(R_2O)_t(G)_v$    (IV)

wherein:
$R_1$ is chosen from a saturated or unsaturated, linear or branched alkyl group comprising from 8 to 24 carbon atoms, or an alkylphenyl group wherein the linear or branched alkyl group comprises from 8 to 24 carbon atoms,
$R_2$ represents an alkylene group comprising from 2 to 4 carbon atoms,
G represents a saccharide unit comprising from 5 to 6 carbon atoms,
t is a number ranging from 0 to 10, and
v is a number ranging from 1 to 15.
12. The composition according to claim 1, wherein the nonionic surfactant is present in an amount ranging from about 0.1% to about 10% by weight, relative to the total weight of the composition.
13. The composition according to claim 1, wherein the total amount of surfactant ranges from about 5.5% to about 30% by weight, relative to the total weight of the composition.
14. The composition according to claim 1, wherein the at least one cationic polymer is present in an amount ranging from about 0.05% to about 10% by weight, relative to the total weight of the composition.
15. The composition according to claim 1, further comprising at least one silicone, present in an amount ranging from about 0.05% to about 10% by weight, relative to the total weight of the composition.
16. The composition according to claim 1, wherein the weight ratio of the surfactant of carboxylate type and the surfactant of acylisethionate type ranges from 0.7 to 2.

17. The composition according to claim 1, wherein the weight ratio of the surfactant of carboxylate type and the surfactant of acylisethionate type ranges from 0.6 to 1.7.

18. The composition according to claim 1, wherein the weight ratio of the surfactant of carboxylate type and the surfactant of acylisethionate type ranges from 1.3 to 2.

19. The composition according to claim 1, wherein the weight ratio of the surfactant of carboxylate type and the surfactant of acylisethionate type ranges from 1.3 to 1.7.

20. The composition according to claim 1, wherein the at least one anionic surfactant of carboxylate type is chosen from palmitoylsarcosinates, stearoylsarcosinates, lauroylsarcosinates and cocoylsarcosinates and mixtures thereof.

* * * * *